United States Patent
Takahashi et al.

(10) Patent No.: US 9,097,514 B2
(45) Date of Patent: Aug. 4, 2015

(54) DEVICE AND METHOD FOR INSPECTING TYRE SHAPE

(75) Inventors: Eiji Takahashi, Kobe (JP); Naokazu Sakoda, Kobe (JP); Toshiyuki Tsuji, Kobe (JP); Hajime Takeda, Takasago (JP); Masao Murakami, Takasago (JP)

(73) Assignee: Kobe Steel, Ltd., Hyogo (JP)

( * ) Notice: Subject to any disclaimer, the term of this patent is extended or adjusted under 35 U.S.C. 154(b) by 471 days.

(21) Appl. No.: 13/514,285

(22) PCT Filed: Dec. 2, 2010

(86) PCT No.: PCT/JP2010/007038
§ 371 (c)(1), (2), (4) Date: Jun. 6, 2012

(87) PCT Pub. No.: WO2011/070750
PCT Pub. Date: Jun. 16, 2011

(65) Prior Publication Data
US 2012/0242824 A1    Sep. 27, 2012

(30) Foreign Application Priority Data

Dec. 7, 2009   (JP) ................................ 2009-277667
Mar. 24, 2010  (JP) ................................ 2010-068107

(51) Int. Cl.
*H04N 7/18*    (2006.01)
*G01B 11/06*   (2006.01)
(Continued)

(52) U.S. Cl.
CPC ......... *G01B 11/0608* (2013.01); *G01M 17/027* (2013.01); *G01N 21/95* (2013.01); *G06T 7/001* (2013.01); *G06T 2207/30164* (2013.01)

(58) Field of Classification Search
None
See application file for complete search history.

(56) References Cited

U.S. PATENT DOCUMENTS 6,539,789 B1 *   4/2003   Kostka et al. .................... 73/146
7,012,701 B2 *   3/2006   Hassler et al. ................. 356/601
(Continued)

FOREIGN PATENT DOCUMENTS

JP   05-187843   7/1993
JP   10-160452   6/1998
(Continued)

OTHER PUBLICATIONS

International Preliminary Report on Patentability for corresponding International Application No. PCT/JP2010/007038, Jul. 19, 2012.
(Continued)

*Primary Examiner* — Jorge L Ortiz Criado
*Assistant Examiner* — Stefan Gadomski
(74) *Attorney, Agent, or Firm* — Studebaker & Brackett PC

(57) ABSTRACT

Boundary lines which are contours of uneven marks are detected in a sample original image of the sidewall surface of a sample tire, and a mask image showing the position of the boundary lines is generated. Thereupon, a height offset image which shows a height of the uneven marks is generated by, in use of a plurality of discrete height threshold values, classifying the height of regions in the sample original image which remain after excluding regions corresponding to the positions of the boundary lines shown in the mask image. An unevenness-excluded image is generated by excluding the uneven marks from an inspection image of a sidewall surface of a tire under inspection, by subtracting the height offset image from the inspection image. A shape defect in the sidewall surface of the tire under inspection is inspected on the basis of the unevenness-excluded image.

13 Claims, 8 Drawing Sheets

(51) Int. Cl.
*G01M 17/02* (2006.01)
*G01N 21/95* (2006.01)
*G06T 7/00* (2006.01)

(56) References Cited

U.S. PATENT DOCUMENTS

| | | |
|---|---|---|
| 7,343,789 B2 | 3/2008 | Fujisawa et al. |
| 2007/0209431 A1 | 9/2007 | Fujisawa et al. |
| 2008/0218742 A1 | 9/2008 | Sakoda et al. |
| 2010/0026799 A1 | 2/2010 | Fujisawa et al. |

FOREIGN PATENT DOCUMENTS

| | | |
|---|---|---|
| JP | 2005-331274 | 12/2005 |
| JP | 2006-284471 | 10/2006 |
| JP | 2008-064486 | 3/2008 |
| JP | 2008-111671 | 5/2008 |
| JP | 2008-221896 | 9/2008 |

OTHER PUBLICATIONS

International Search Report for corresponding International Application No. PCT/JP2010/007038, Jan. 18, 2011.

\* cited by examiner

HEIGHT IMAGE

INVERTED MASK IMAGE

MASK RANGE

MASK RANGE EXCLUDED (MASKED HEIGHT IMAGE)

LINEAR INTERPOLATION OR AVERAGE INTERPOLATION

LINEAR INTERPOLATION  AVERAGE INTERPOLATION

ENVELOPE INTERPOLATION

WINDOW

DEVICE AND METHOD FOR INSPECTING TYRE SHAPE

TECHNICAL FIELD

The present invention relates to tyre inspection technology, and more particularly, to a tyre shape inspection method and a tyre shape inspection device in use of an image processing technique to inspect a shape defect in a sidewall surface in which uneven marks are formed.

BACKGROUND ART

A tyre has a structure composed by layering together various materials, such as rubber, chemical fibers, steel cords, and the like. If there is an irregular portion in this laminated structure, then a protuberance (convex portion) known as a "bulge", or a recess (concave portion) known as a "dent" or "depression", occurs in a portion which has relatively weak pressure resistance, when the tyre is filled with air. Upon inspection, a tyre in which a shape defect, such as a bulge or dent of this kind, has occurred must be excluded from shipment, due to safety problems and problems of external appearance.

Therefore, in a final step of tyre manufacturing (an inspecting step after vulcanization of the tyre material), the tyre surfaces, and in particular the side wall surfaces of the tyre, are inspected for irregular shape defects. Indicator marks (marks constituted by normal unevennesses) which indicate the model and size of the product, and the makers logo, etc., are formed in the sidewall surfaces of a tyre. Therefore, in a shape defect inspection process for a sidewall surface, it is necessary to ensure that these indicator marks are not mistakenly detected as shape defects.

Conventionally, an inspection for irregular shape defects of this kind has been carried out manually, by visual inspection and tactile inspection, but in recent years, automated technology, such as laser ranging sensors, three-dimensional shape measurement devices and camera-based image inspection, and the like, and inspection technology which is not affected by marks formed by normal unevennesses, has been incorporated into the field.

For example, Patent Document 1 discloses a tyre shape detection device which detects a surface shape of a tyre by capturing an image of a line light beam irradiated onto the surface of the tyre while the tyre rotates relatively, and performing shape detection using a light-section method, on the basis of the captured image. This device comprises line light beam irradiating means for irradiating a plurality of line light beams in continuous fashion from a direction that is different to a detection height direction in one light-section line, so as to form the one light-section line on the surface of the tyre, and imaging means for capturing images in a direction in which respective main light beams of the plurality of line light beams irradiated onto the surface of the tyre are reflected regularly with respect to the surface of the tyre.

In particular, this tyre shape detection device detects a tyre surface shape by irradiating a plurality of line light beams in continuous fashion onto the tyre surface and capturing images of the plurality of line light beams thus irradiated.

Furthermore, Patent Document 2 discloses a method of inspecting a three-dimensional shape of one or more figures formed by unevennesses in a tyre surface. This method comprises a step of acquiring unevenness distribution data by measuring an unevenness height in relation to various surface area elements including these figures in a prescribed tyre surface region, a step of identifying a tyre surface portion corresponding to a model figure, in the tyre surface region, on the basis of three-dimensional shape data of the model figure which is previously prepared as a template of the figure and the acquired unevenness distribution data, and a step of determining a degree of matching between the unevenness distribution data of the identified tyre surface portion and the three-dimensional data of the model figure, in respect of each figure, and judging the acceptance or rejection of the three-dimensional shape of the figure of the basis of this degree of matching.

In particular, this method of inspecting tyre unevenness figures is a technique for inspecting defects by calculating a degree of matching between three-dimensional unevenness distribution data obtained by irradiating sheet light onto a tyre surface and three-dimensional shape data of a model figure created from CAD data. In this technology, the suitability or unsuitability of the normal uneven figures (text, etc.) themselves is judged, and therefore a model figure previously prepared as a template of a normal uneven figure is used as teaching data. The template is created from tyre CAD data or mold CAD data.

Patent Document 1: Japanese Patent Application Laid-open No. 2008-221896

Patent Document 2: Japanese Patent Application Laid-open No. 2005-331274

In the tyre shape detection device according to Patent Document 1, it is possible to detect the surface shape of a tyre by a light-section method, and therefore the shape of unevennesses in the tyre surface can be detected. However, it is not possible to tell whether a detected shape of unevennesses in the tyre surface is a normal figure which is formed in the tyre surface, or a defect. Moreover, if there is a defect at the position of a normal figure, then it becomes even more difficult to detect that defect.

Therefore, by creating teaching data (reference data) using the tyre CAD data or mold CAD data as disclosed in Patent Document 2, it might be possible to obtain values which are not affected by deformation or defects in the tyre, and to avoid the difficulties of the technology disclosed in Patent Document 1. However, since tyres are products made of rubber and since tyres are inspected in an inflated state in the tyre shape inspection which is the subject of the invention in Patent Document 1, then there is a large amount of deformation in the tyre with respect to the CAD data. For this reason, an enormous volume of calculations and computations is required just to match the coordinates of the CAD data with the corresponding coordinates on the tyre, and therefore the method in Patent Document 2 is difficult to apply practically.

Moreover, a method which uses actually measured tyre height data as teaching data can readily be inferred from the method using CAD data which is disclosed in Patent Document 2. According to this method, it is possible to acquire actual height data, in a simple fashion.

However, in this case, the tyre height image which is used as teaching data must contain only normal uneven figures, and must be completely free of irregular defects (bulges/dents) which are the object of detection, or height variations caused by "runout" components, which are large undulating deformations in the tyre circumference direction. If height image data which contains irregular defects that are the object of detection, or runout components, is used as teaching data, then although normal uneven marks, such as text, are planarized (excluded) by difference processing during on-line inspection, the irregular defects and runout components present in the teaching data will be transferred to the height image under inspection, and hence height image data of this kind cannot be used as teaching data for inspection. Furthermore, it is not practicable to manufacture a perfectly smooth tyre which is free of runout components, for the express purpose of registering teaching data.

SUMMARY OF THE INVENTION

Therefore, the present invention was devised in view of the aforementioned problems, an object thereof being to provide a tyre shape inspection method and a tyre shape inspection device whereby an irregular defect in a sidewall surface can be inspected without being affected by marks (text, logos, patterns, etc.) constituted by normal unevennesses that are present in the sidewall surface of the tyre.

The tyre shape inspection method according to the present invention inspects a shape defect in a sidewall surface of a tyre under inspection, using an image of a sidewall surface of a sample tyre having the sidewall surface in which uneven marks are formed. The tyre shape inspection method includes a teaching operation step and an inspection operation step. The teaching operation step includes: a mask image generating step of detecting boundary lines which are contours of the uneven marks, in a sample original image which is a two-dimensional image of the sidewall surface of the sample tyre, and generating a mask image showing the positions of the boundary lines; and a height offset image generating step of generating a height offset image which shows a height of the uneven marks, the height offset image being obtained by, in use of a plurality of discrete height threshold values, classifying a height of regions in the sample original image which remain after excluding regions corresponding to the positions of the boundary lines shown in the mask image; and the inspection operation step includes: a difference processing step of excluding the uneven marks from an inspection image which is a two-dimensional image of the sidewall surface of the tyre under inspection to generate an unevenness-excluded image, by subtracting the height offset image from the inspection image; and a shape defect inspecting step of inspecting the shape defect in the sidewall surface of the tyre under inspection, on the basis of the unevenness-excluded image obtained as a result of the difference processing step.

DESCRIPTION OF EMBODIMENTS

Below, embodiments of the present invention are described with reference to the drawings.

The tyre shape inspection device 1 relating to an embodiment of the present invention measures heights of various locations on a tyre T, by capturing an image of line light beam which is irradiated onto a surface of the rotating tyre T, with a camera, and performing shape detection using a light-section method on the basis of this captured image. Thereupon, the tyre shape inspection device 1 substitutes the measured heights of the locations on the tyre T with respectively corresponding brightness values to obtain a two-dimensional image (inspection image) of the surface of the tyre T.

Moreover, the tyre shape inspection device 1 excludes indicator marks formed on the sidewall surface of the tyre T, on the basis of the "inspection image" of the tyre T described above, and a "mask image" and "height offset image" of a sample type (a tyre free of defects), and then inspects a defect present on the surface of the tyre T. The "mask image" and the "height offset image" are created by using a "sample original image" which is obtained by capturing an image of a sample tyre. The details of the "sample original image", the "mask image" and the "height offset image" are described hereinafter.

In the case of shape inspection of a tyre T, the measurement object may be the tread surface and the sidewall surfaces of the tyre T, but in the present embodiment, the sidewall surface is taken to be the measurement object.

Figure 2:
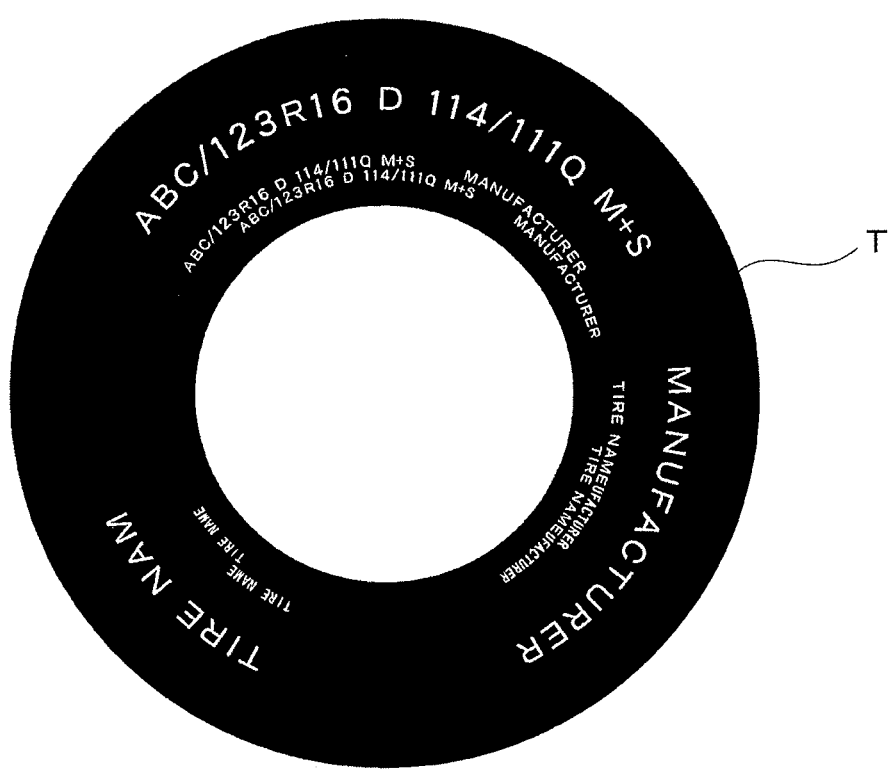
FIG. 2 is a schematic drawing showing a sidewall surface of a tyre.

As shown in FIG. 2, the sidewall surface of a tyre T is a portion between the tread surface which makes contact with a road surface and a bead portion which is fitted into a wheel rim. In FIG. 2, the portions marked in white are indicator marks (normal figures, such as text, logos, patterns, etc.) which are formed on the sidewall surface, and these can be regarded as "normal uneven marks". These normal uneven marks are formed by unevennesses having a prescribed height with respect to the portion (base surface) of the sidewall surface where normal uneven marks are not formed.

Firstly, the general composition of the tyre shape inspection device 1 relating to the embodiment of the present invention will be described with reference to FIGS. 1A and 1B.

Figure 1A:
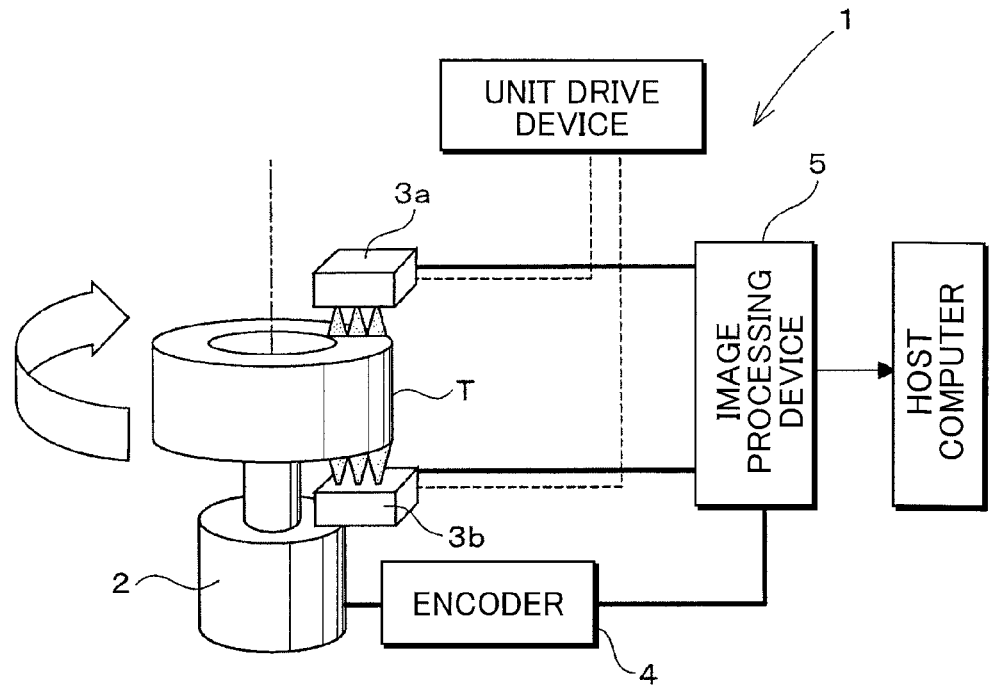
FIG. 1A is a schematic drawing showing a composition of a tyre shape inspection device according to an embodiment of the present invention.

As shown in FIG. 1A, the tyre shape inspection device 1 comprises a tyre rotating machine 2, a sensor unit (imaging unit) 3 (3a, 3b), encoder 4, an image processing device 5, and the like.

The tyre rotating machine 2 is a rotating device equipped with a motor, and the like, that rotates a tyre T that is the object of shape inspection, about a rotational axle thereof. The tyre rotating machine 2 rotates the tyre T for example at a speed of 60 rpm. During this rotation, the surface shape of the sidewall surface in a range covering the entire circumference of the tyre is detected by the sensor unit 3, which is described hereinafter.

In the present embodiment, the tyre shape inspection device 1 includes two sensor units 3 (3a, 3b) which are used respectively for shape measurement of the two sidewall surfaces of the tyre T. The sensor units 3a, 3b are units which each incorporate a line light beam irradiating unit for irradiating line light beam (a light-section beam) onto the surface of the rotating tyre T, and an imaging camera 6 which captures an image of the line light beam reflected at the surface of the tyre T.

Figure 1B:
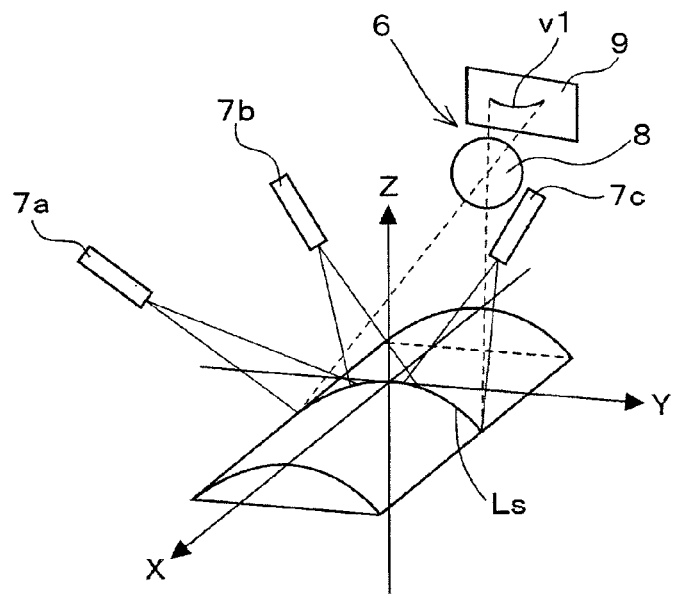
FIG. 1B is a schematic drawing showing a three-dimensional arrangement of a line light beam irradiating unit and a camera in a sensor unit provided in the tyre shape inspection device.

FIG. 1B is a diagram showing a schematic view of the arrangement of the equipment provided in the sensor unit 3. In FIG. 1B, the Y axis indicates the radius direction of the tyre T, which has a circular shape, at the shape detection position of the tyre T. The Z axis indicates the detection height direction from the sidewall surface at the shape detection position of the tyre T (the height direction of the surface being detected). The X axis indicates a direction orthogonal to the Y axis and the Z axis. In other words, in a sensor unit 3 which is used for shape detection of the sidewall surface of the tyre T, the Z axis is a coordinates axis parallel to the axis of rotation of the tyre T, and the Y axis is a coordinates axis which represents a direction normal to the axis of rotation of the tyre T. The correspondence between the tyre T and the coordinates axes may be varied in accordance with the mode of supporting the camera 6.

The line light beam irradiating unit comprises a plurality of line light beam sources 7a, 7b, 7c (in FIG. 1B, three line light beam sources are depicted). The line light beam irradiating unit is a device which irradiates a plurality of line light beams from the line light beam sources 7a, 7b, and 7c so as to faun one light-section beam on a single line Ls on the surface of the tyre T. The plurality of line light beams are irradiated from different directions to the detection height direction (Z axis direction), in the single line Ls (light-section beam). The plurality of line light beams are irradiated so as to be continuous on the single line Ls.

Furthermore, the imaging camera 6 comprises a camera lens 8 and an imaging element 9, and captures an image v1 of the plurality of line light beams which are irradiated in continuous fashion onto the sidewall surface of the tyre T (an image of the light-section beam on the single line Ls).

On the other hand, an encoder 4 is provided in the tyre rotating machine 2. This encoder 4 is a sensor which detects an angle of rotation of a rotational axle of the tyre rotating machine 2, in other words, an angle of rotation of the tyre T, and outputs the detected angle of rotation as a detection signal. This detection signal is used to control the image capture timing of the imaging cameras 6 provided in the sensor units 3a, 3b.

For example, the image processing device 5 receives a detection signal output from the encoder 4 each time the tyre T rotating at a speed of 60 rpm turns through a prescribed angle, and controls the unit drive device in FIG. 1 in such a manner that the shutters of the imaging cameras 6 of the sensor units 3a, 3b is released in accordance with the reception timing of the detection signals. By this means, imaging is performed at a prescribed imaging rate matched to the reception timing of the detection signal.

Apart from the aspect shown in FIG. 1, it is also possible to adopt a aspect in which an image processing device 5 is incorporated respectively into each of the sensor units 3a and 3b. In this case, for instance, control signals from the unit drive device and rotational speed pulse signals from the encoder 4 are input to each sensor unit 3a, 3b, and the final results are output respectively to the host computer from each of the sensor units 3a, 3b. Furthermore, in this case, the unit drive device does not need to perform a role of outputting an instruction to release the shutter, and may also have a role of outputting commands such as a laser switch-on instruction or a measurement start instruction, to the sensor units 3a, 3b, for instance. It is also possible to adopt a aspect in which the instruction for releasing the shutter is controlled by the image processing device 5 incorporated into each of the sensor units 3a, 3b, in accordance with the amount of movement produced by rotation of the tyre T, by synchronizing with the pulse signal from the encoder 4.

The signals (one-line images) from the sensor units 3a, 3b are input to the image processing device 5. The image processing device 5 obtains height distribution information about the portion onto which the light-section beam has been irradiated (one line portion on the sidewall surface), by applying a triangulation method to the input one-line image. Thereupon, the image processing device 5 substitutes the heights of each of the measured locations on the surface of the tyre T with corresponding brightness values, stores the brightness values in an in-built frame memory (imaging memory), and thereby obtains a two-dimensional image (inspection image) of the surface of the tyre T.

This two-dimensional image (inspection image) is information in which the surface height measurement values (brightness values) of each location in the full range (360° range) of the circumference direction of the sidewall surface are arranged in a two-dimensional coordinates system based on a Y axis which represents the radius direction of the tyre T and an X axis (frame) which represents the circumference direction of the tyre T.

Figure 7A:
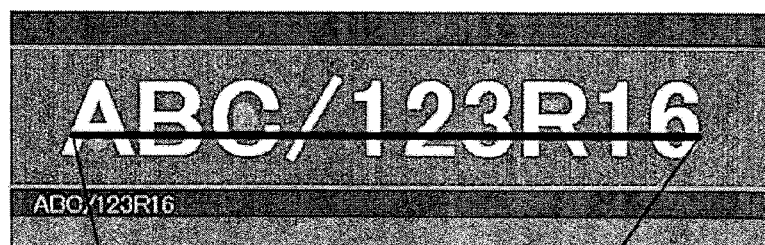
FIGS. 7A to 7C are schematic drawings showing a method of determining discrete height threshold values in a tyre shape inspection method according to an embodiment of the present invention.
Figure 7B:
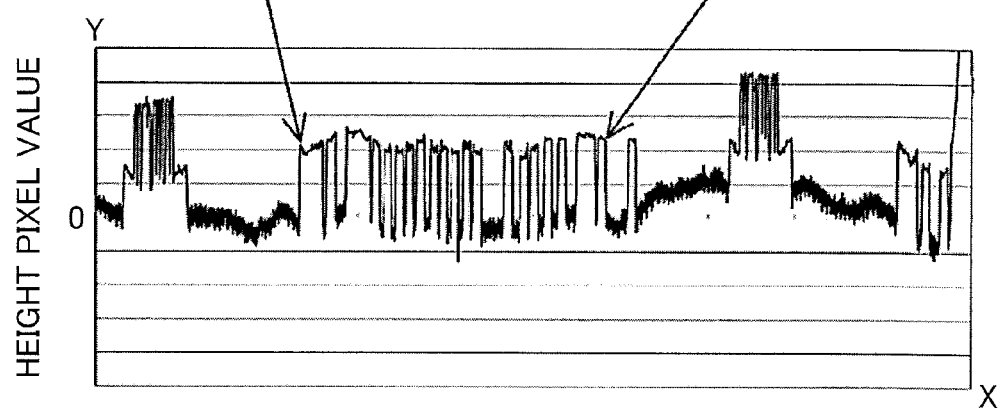

The graph shown in FIG. 7B corresponds to the height distribution information and the image illustrated in FIG. 7A corresponds to the inspection image or sample original image. There is a one-to-one correspondence between the value on the vertical axis in the height distribution information (height pixel value), and the brightness value of the inspection image, and these values are used synonymously in the description given below.

Moreover, the image processing device 5 according to the present embodiment is able to inspect irregular defects present in abnormal uneven mark portions of the sidewall surface of the tyre, on the basis of the obtained inspection image and the height distribution information corresponding to one line in the inspection image, by excluding only the normal uneven marks from the inspection image and applying a known image processing method to the image after this exclusion. The image processing device 5 is achieved by hardware constituted by a personal computer, for example.

Next, processing which is carried out by the image processing device 5 of the tyre shape inspection device 1 of the present embodiment will be described.

Figure 3:
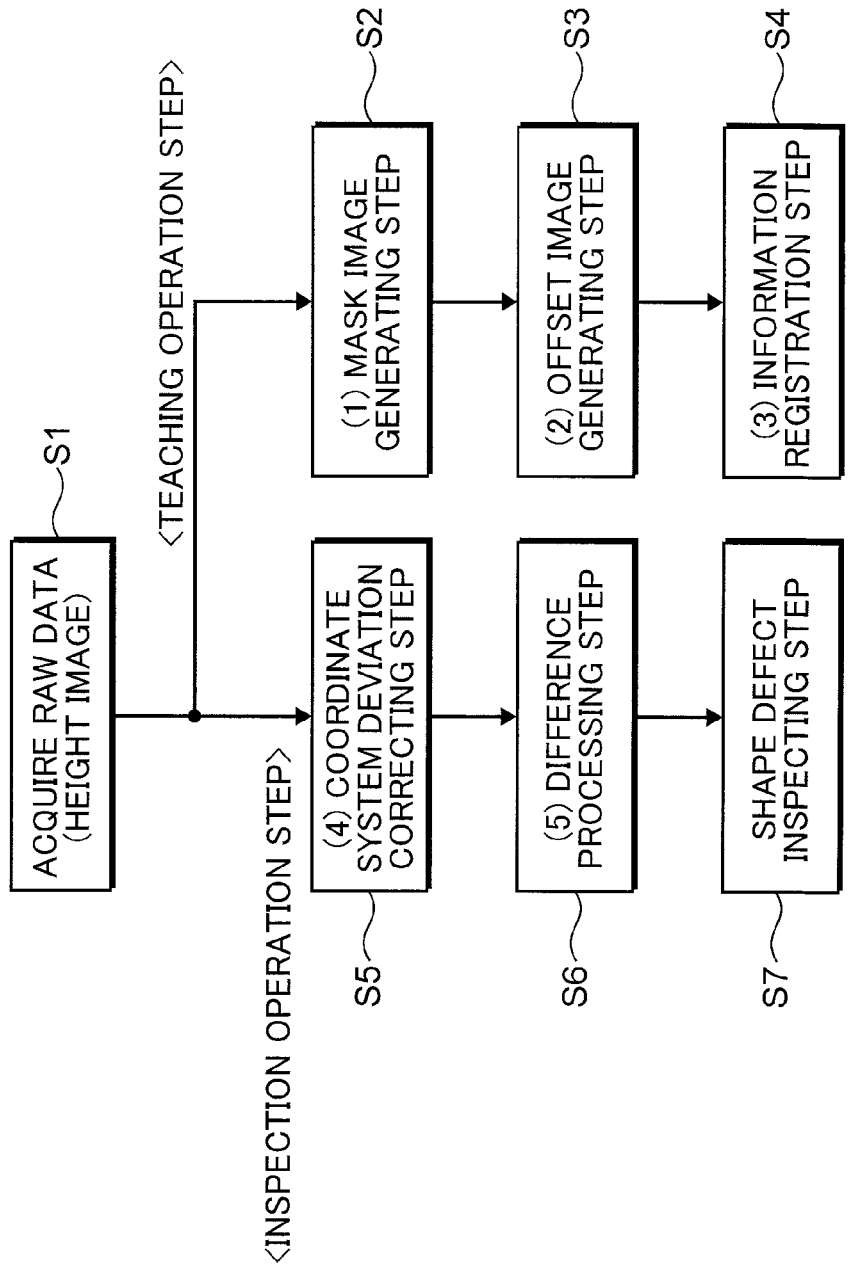
FIG. 3 is a flowchart showing contents of processing in a tyre shape inspection method according to an embodiment of the present invention.

FIG. 3 is a flowchart showing the contents of processing which is carried out by the image processing device 5. As is clear from FIG. 3, the processing carried out by the image processing device 5 includes a "inspection operation step" of performing on-line inspection for irregular defects present on the sidewall surface of the tyre. Moreover, this processing includes a "teaching operation step", as a preliminary step before the inspection operation step.

The inspection operation step includes a "difference processing step (S6)" and a "shape defect inspecting step (S7)". In the difference processing step (S6), the height offset image is subtracted from the inspection image, which is a two-dimensional image of the sidewall surface of the tyre under inspection, and furthermore the boundary regions shown in the mask image are also excluded. The respective steps S6, S7 are carried out by a difference processing unit and a shape defect inspecting unit provided in the image processing device 5, wherein in the shape defect inspecting step (S7), a shape defect in the sidewall surface of the tyre under inspection is inspected on the basis of a normal uneven mark-excluded image which is obtained as a result of the difference processing step (S6).

As illustrated in FIG. 3, the teaching operation step includes a "mask image generating step (S2)" and a "height offset image generating step (S3)". In the mask image generating step (S2), boundary lines which are the contours of normal uneven marks are detected in the sample original image, which is a two-dimensional image of the sidewall surface of the sample tyre, and a mask image showing the positions of the boundary lines is generated. In the height offset image generating step (S3), a height offset image which shows the height of the normal uneven marks is generated, this image being obtained by using a plurality of discrete height threshold values to classify the height of the regions in the sample original image which remain after excluding the regions corresponding to the positions of the boundary lines shown in the mask image. These steps S2, S3 are carried out by a mask image generating unit and a height offset image generating unit which are provided inside the image processing device 5.

Usually, since there are a plurality of types of tyre which are the object of inspection, then a set-up operation is carried out as a registration operation before on-line inspection, for each type of tyre (each TyreID). This set-up operation is an operation for registering, prior to inspection, design information relating to the tyre shape, such as the tyre diameter, the width of the ground contact surface (tread surface), and the like, which differs with each TyreID, and this operation is essential in case that there is a plurality of types of tyres. In the tyre shape inspection according to the present embodiment, the set-up operation described above is carried out prior to the inspection operation step.

Especially notable characteristics of the tyre shape inspection method according to the present embodiment are the "difference processing step (S6)" in the inspection operation step, and the "mask image generating step (S2)" and the "height offset image generating step (S3)" in the teaching operation step. These steps will be mainly described below. Firstly, the teaching operation step will be described in detail with reference to FIG. 4.

Firstly, the height image (raw data) of the sidewall surface of a sample tyre, which is an ideal tyre that is free of defects, is obtained. The obtained height image (raw data) may include "undetected points". An undetected point is a point at which a height coordinate cannot be obtained, because the sheet light does not return to the camera due to the effects of step differences of the normal uneven marks, and hence the received light intensity is equal to or lower than a specified value. A height coordinate of 0 (black point) is output for these undetected points. Thereupon, linear interpolation values are calculated by using the height coordinates of two pixels in the vicinity of the undetected point, for which the height coordinates have been detected, the two pixels being aligned in the tyre circumference direction on either side of the undetected point. The linear interpolation value thus calculated is applied as a coordinate for the undetected point.

The method of determining the coordinate of an undetected point is not limited to this. For example, it is possible to determine the coordinate of an undetected point by a method of directly copying the height in the vicinity of the undetected point (zero-order approximation), or by planar interpolation through forming a plane based on four points surrounding the undetected point (two points in the circumference direction and two points in the radius direction), or the like. If the height coordinates of undetected points are left unspecified, then caution is required because large differential values occur unexpectedly in the subsequent smooth differentiation processing, and there is a possibility of causing adverse effects on the final detection of the positions (boundary lines) of the normal uneven marks.

Since a low-order curved component is generally present in the tyre in radius direction, then the height image after the linear interpolation described above includes a low-order curved component in the tyre radius direction and the tyre circumference direction. If the next smooth differentiation processing step is carried out without removing this curved component, then the differential values become higher as a result of the curved component. The differential values caused by the curved component may be difficult to distinguish from the differential values of the boundary lines of the normal uneven marks, which are the actual object of detection. Therefore, desirably, a planarization process is carried out to exclude the curved component from the height image after linear interpolation.

This low-order curved component which is predicted to reflect the tyre design CAD data or the mold CAD data can be corrected by using a shape model from these CAD data. However, in general, coordination with CAD data is difficult systematically, and in the present embodiment, an ideal curved component is obtained from the acquired height image itself.

Firstly, an average cross-sectional profile shape in the curved component direction is determined. For example, the curved component is mathematically modeled by least-squares fitting based on a secondary curve of the cross-sectional profile shape, and the mathematically modeled curved component is excluded from the height image after the linear interpolation described above.

Figure 5:
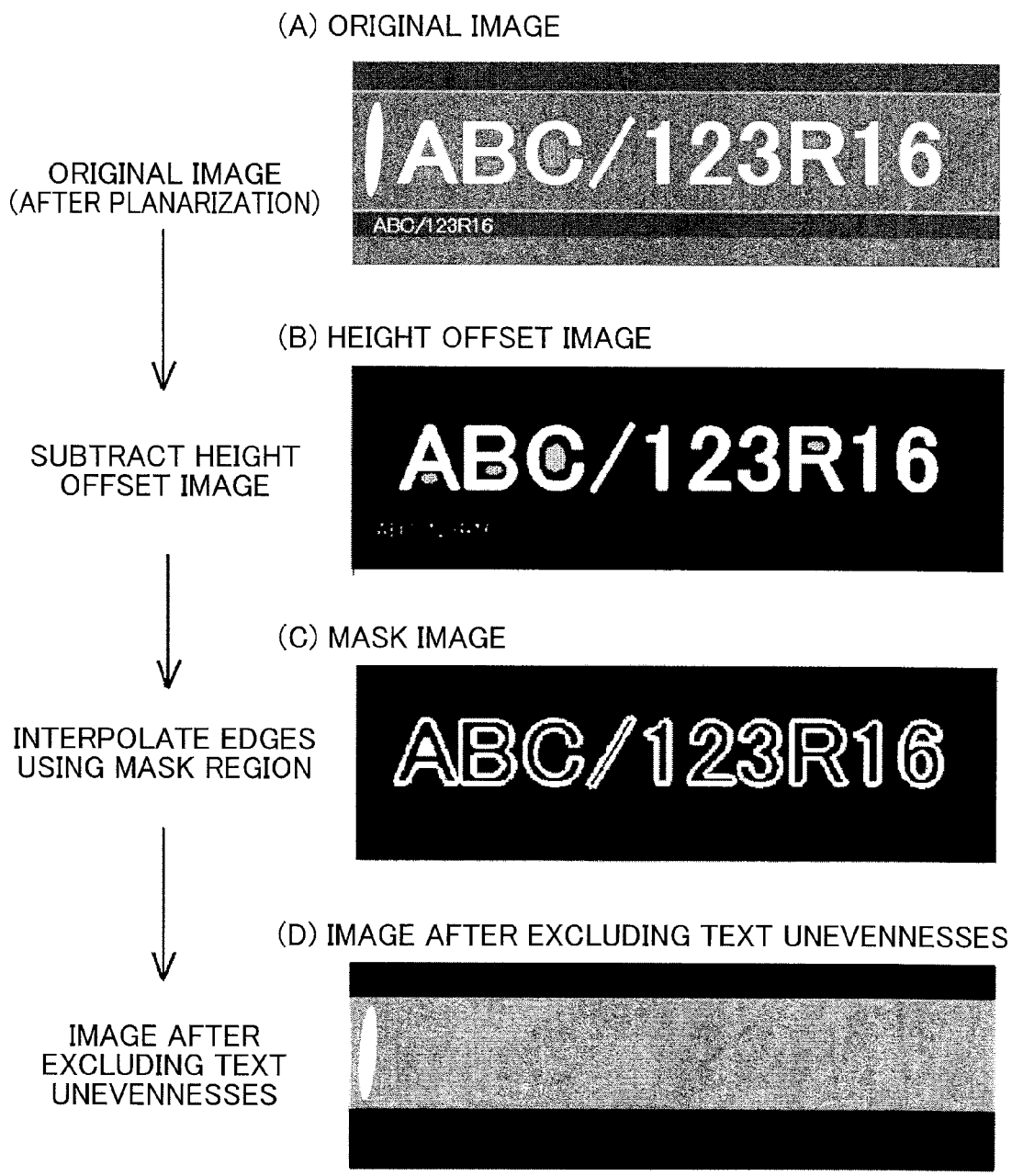
FIG. 5 is a schematic drawing showing steps of image processing in a tyre shape inspection method according to an embodiment of the present invention.

By this means, the height image after linear interpolation is planarized with a high degree of accuracy, while leaving uneven figures, such as circumferential figures which have a height coordinate that varies throughout the circumference. By this means, the sample original image shown in FIG. 5(A) is obtained (S21).

Figure 4A:
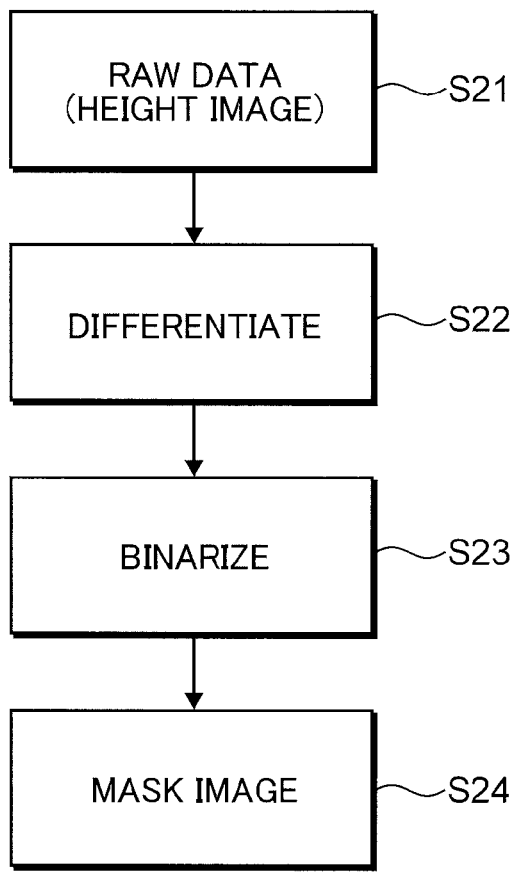
FIG. 4A is a flowchart showing a mask image generation process in a tyre shape inspection method according to an embodiment of the present invention.

Next, the mask image generating step (S2) in FIG. 3 will be described. In FIG. 4A, this mask image generating step (S2) is shown as a mask image generating flowchart.

An image of differential values is obtained (S22) by applying a differential filter (two-dimensional smoothing differentiation filter) using a Sobel filter or Laplacian filter, for instance, to the planarized height image (called the "sample original image" below) which was obtained by the processing (S21) described above.

An average value (Ave) and a variance ($1\sigma$) are determined for each line, in the image of differential values thus obtained. The average value (Ave) and the variance ($1\sigma$) thus determined are used to determine a binarization threshold value which can serve to separate the boundary lines of the normal uneven marks from differential values due to background noise. The image of differential values is binarized on the basis of this binarization threshold value. By this means, a binarized image showing the boundary lines of the normal uneven marks is obtained (S23).

Preferably, isolated pixel points in the binarized image thus obtained are excluded by an isolated point removal filter, and furthermore, processing is carried out to expand the boundary line portions of the normal uneven marks in the image obtained by removing the isolated pixel points, using an dilation filter.

The image obtained by the processes described above is a mask image in which the value of binary image points in the boundary line portions is 1 and the value of the binary image points in the portions apart from the boundary lines is 0. An image of this kind is shown in FIG. 5(C). This mask image is saved in an internal memory of the image processing device 5 (S24).

Figure 4B:
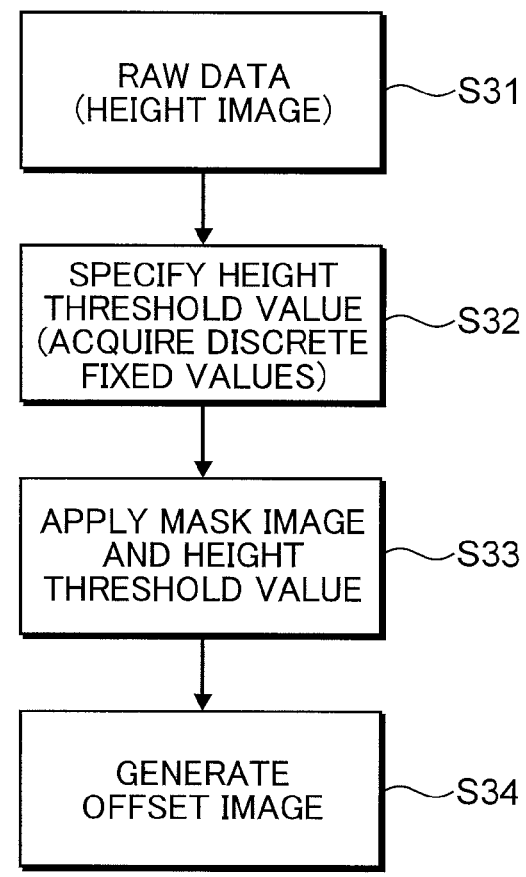
FIG. 4B is a flowchart showing an offset image generation process in the tyre shape inspection method according to an embodiment of the present invention.

Next, the height offset image generating step (S3) in FIG. 3 will be described with reference to FIG. 4, FIG. 6 and FIG. 7. In FIG. 4B, this height offset image generating step (S3) is shown as an offset image generating flowchart. In the present step, similarly to the mask image generating step (S2), a sample original image which has been subjected to linear interpolation and a planarization process is used (S31).

The portion indicated by the solid line in the sample original image after planarization, which is shown as a schematic drawing in FIG. 7A, indicates a normal uneven mark portion which is one part of a phase adjustment line in the single line described above. The graph in FIG. 7B shows a height pixel profile (cross-sectional shape) of a phase adjustment line of the schematic single line such as that shown in FIG. 7A. It can be seen that in this profile, there is an overall low-frequency variation in the height pixels (low-frequency component), which is the undulation of the sidewall surface, and in the portions of the normal uneven marks, there are sudden changes in the height pixel values. The low-frequency height pixel variation is a variation displaying a low frequency of approximately the 20th to 70th order (approximately the 20th to 70th order after discrete Fourier transform).

Here, the phase adjustment line will be described. During the set-up operation (during teaching), final set-up data (teaching data) is acquired and recorded in the device by the image processing described in the present embodiment, on the basis of the height image (raw data) of the sidewall surface of a sample tyre which is a tyre that is free of defects. During inspection of a tyre, the tyre rotates through a different angle to the set-up operation, and a phase difference is calculated from the shape differences of the two images on the "phase adjustment line", in order to match the phase of the image under inspection (the angle=the difference in the angle of rotation among 360°) with the recorded set-up data. Any desired line used for this purpose (for example, a line designated in set-up) is called a phase adjustment line.

In the height pixel profile indicated by the graph in FIG. 7B, the portion corresponding to the solid line portion of the sample original image in FIG. 7A is indicated by the arrows. The respective normal uneven marks shown here are of substantially the same height, but since they are located (formed) on the low-frequency height pixel variation (runout component) described previously, then they have respectively different heights depending on this low-frequency pixel height variation. This is described in further detail here with reference to the graph in FIG. 7C.

Figure 7C:
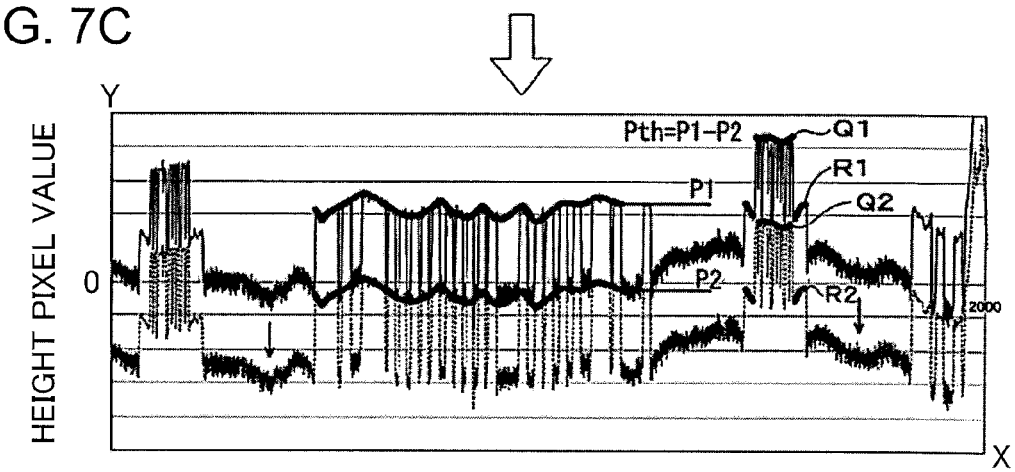

The thick solid line P1 in FIG. 7C shows the low-frequency height pixel variation (runout component) in the surface portion of the normal uneven marks. If the height pixel profile including the portion indicated by this thick solid line P1 is offset in the negative direction along the vertical axis, then in the vicinity of the height pixel value 0, the thick solid line P1 is substantially continuous with the runout component (base runout component) in the portions apart from the normal uneven marks in the original height pixel profile. For instance, it can be seen that, if the height pixel profile is offset in such a manner that the thick solid line P1 moves to the position of the thick solid line P2, then the low-frequency height pixel variation (runout component) in the surface portion of the normal uneven marks is substantially continuous with the base runout component. The difference (P1−P2) between the thick solid line P1 and the thick solid line P2 in this case forms a fixed height value (height threshold value) Pth.

On the other hand, the thick solid line Q1 which indicates the low-frequency height pixel variation (runout component) in the surface portion of the normal uneven mark adjacently to the right of P1 is offset to the position of the thick solid line Q2, and the thick solid line R1 is offset to the position of the thick solid line R2. In this case, the thick solid line Q2 and the thick solid line R2 after offset are not continuous with the base runout component. Therefore, the amount of offset of the height profile is changed in such a manner that the thick solid line R2 is continuous with the base runout component, and another fixed height value is obtained. Moreover, the amount of offset of the height profile is changed in such a manner that the thick solid line Q2 is continuous with the base runout component, and yet another fixed height value is obtained. In a method of this kind, a plurality of discrete height threshold values is obtained (S32).

Presuming that the tyre is one in which normal uneven marks (text, figures, etc.) in the sidewall surface of the tyre are constituted only by height offset values of several types, it can be seen that the procedure described above is an operation for determining a plurality of discrete fixed height values corresponding to these height offset values of several types, from among (on the basis of) a height profile which includes irregular height variation such as a runout component.

The plurality of discrete height fixed values of this kind do not have to be decided commonly for the whole sidewall surface, and may also be determined respectively for each region obtained by dividing the sidewall surface. In a method which divides the sidewall surface into a plurality of regions, for instance, a height image is displayed on display means, and rectangular regions, and the like, are set as the regions for division, by using a GUI (mouse operations, etc.), while manually and visually checking the meaning of the text and the layout of the figures, and the like.

A step of generating a height offset image which indicates the heights of the normal uneven marks using a plurality of discrete fixed height values obtained in this way will be described below.

Figure 6A:
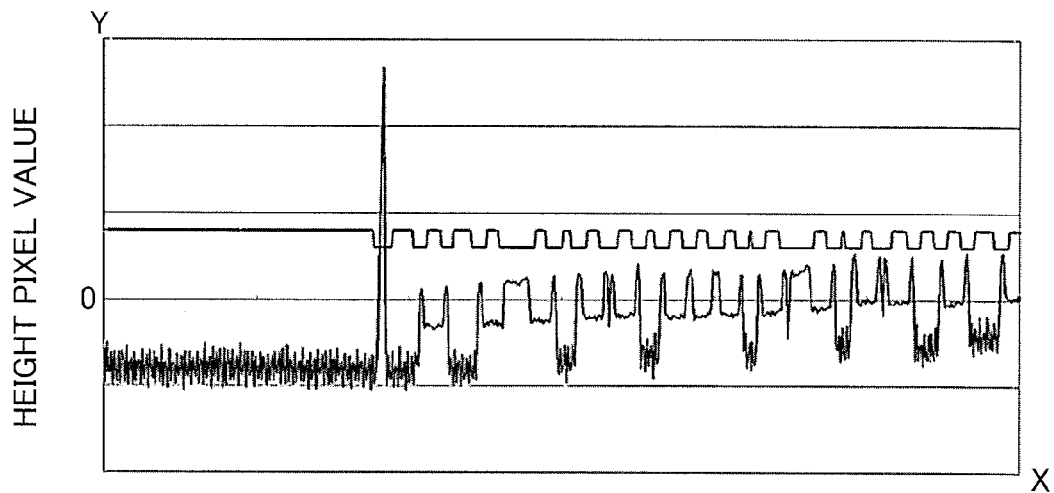
FIGS. 6A and 6B are diagrams showing a relationship between a height pixel profile and a label region in a tyre shape inspection method according to an embodiment of the present invention.
Figure 6B:
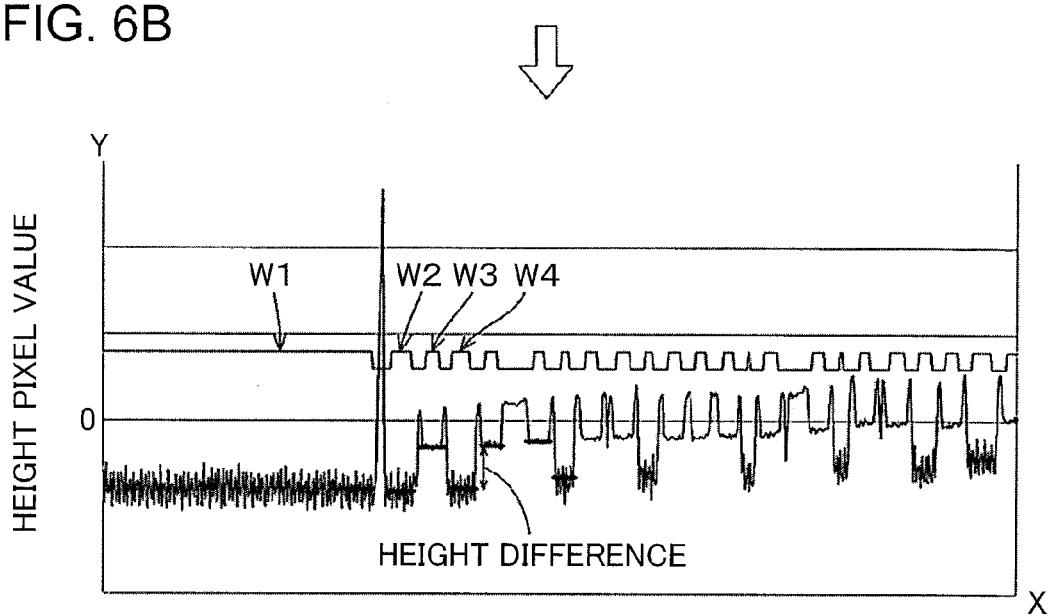

FIGS. 6A and 6B are diagrams showing a relationship between a height pixel profile and a label region in a tyre shape inspection method according to the present embodiment. FIG. 6A is a graph showing an enlarged view of several hundred points along the X coordinate of the tyre circumference direction, in one line of a height profile in the circumference direction of the sidewall as shown in a sample original image. The rectangular waveform in the graph is a part of an inverted mask image which is generated by inverting the mask image determined previously. The rectangular waveform is an image at the same location as the height profile. In the graph, the rectangular waveform is superimposed on the height profile.

The inverted mask image is a rectangular waveform which oscillates between the height pixel values 0 and 1, similarly to the non-inverted mask image. In order to make the graph easier to read, the inverted mask image is moved in the positive direction of the height pixel value (the upward direction on the Y axis).

In the inverted mask image, the value of the binary pixel points in the boundary line portions is 0, and the value of the binary pixel points in the portions other than the boundary lines is 1. Therefore, in FIGS. 6A and 6B, a region corresponding to a height pixel value of 0 in the inverted mask image indicates a boundary line portion of a normal uneven mark. In the inverted mask image, label numbers are allocated respectively to each region corresponding to a height pixel value of 1 which is demarcated by a boundary line portion, and these regions are set as label regions.

The longest label region W1 of these regions (in the case of FIG. 6B, the label region in the leftmost portion of the graph) is recorded as a start region for height offset calculation. Thereupon, the average height pixel value in the longest label region W1, in a portion adjacent to and including the end point which borders the boundary line of the normal uneven mark, is determined from the height profile in FIG. 6B. Thereupon, the average height pixel value in the label region W2 which is adjacent on a side of the boundary line (via the boundary line) is determined. Subsequently, the height difference of the pair of regions constituted by the label region W1 and the label region W2 is calculated. This height difference is the difference between the two height pixel values which are determined as described above. The height offset value of the average height pixel value in the longest label region (calculation start region) W1 is set to zero.

Next, the height difference of the pair of regions constituted by the label region W1 and the label region W2 is compared with the plurality of discrete fixed height values acquired previously, and the fixed height value having the smallest difference with respect to (which substantially matches) this height difference is assigned as the height offset value of the label region W2 which is adjacent to the longest label region W1. In other words, the fixed height value having the smallest difference is allocated as a height offset value of the region W2 which is posterior in the alignment sequence, of the pair of label regions which constitute the pair of regions. The allocated height offset value is recorded in the offset image memory region.

Thereafter, height offset values are respectively allocated in sequence to all of the remaining label regions W3, W4, . . . , by a similar method. In other words, for each of the remaining plurality of pairs of regions, apart from the pair consisting of region W1 and region W2 (for example, a pair of regions consisting of region W2 and region W3, and a pair of regions consisting of region W3 and region W4, or the like), a height difference of the two mutually adjacent regions is determined, and the fixed height value having the smallest difference with respect to the height difference of the pair of regions is allocated as the height offset value of the label region which is posterior in the alignment sequence in the pair of regions (S33).

When height offset values have been allocated to one line throughout the whole circumference of the tyre, height offset values are allocated similarly to other lines throughout the whole circumference, in sequential fashion. By allocating height offset values to the lines in the whole range of the sample original image in this way, the height offset image shown in FIG. 5(B) is obtained (S34).

If there is absolutely no low-frequency runout component in the height image acquired during the teaching process and the normal uneven marks have the same values as the actual tyre design CAD data, then the acquired sample original image (height image) itself is recorded as a height offset image, without using the "plurality of discrete fixed height values", or the determined height differences themselves (the actual height differences between adjacent regions) are set as the relative offset values, without using the "plurality of discrete fixed height values".

However, tyres which are made of rubber and are inflated with air are never free from a runout component, and therefore it is not practical to use the actual acquired sample original image as an offset image. Furthermore, if the determined height differences themselves are recorded as continuous offset values, then errors caused by the runout component accumulate during the measurement of one circumference of the tyre, and hence a problem occurs in that the height offset value at the end point of the line is not continuous with the height offset value at the start point of the line.

Consequently, it is possible to acquire a height offset image for practical teaching by the present method which infers the height of normal uneven marks on the sidewall surface with a prescribed offset, by using a plurality of discrete fixed height values and reflecting the shape of the tyre when in an inflated state.

In the information recording step (S4) in FIG. 3, the mask image and the offset image are recorded in the image processing device 5, and the teaching operation step terminates. By the foregoing, it is possible to check and correct the tyre sample image after the teaching process, on a computer GUI, and hence the teaching operation can be achieved in a short period of time.

After the teaching process described above, an inspection operation step (on-line inspection) is carried out to inspect for irregular defects (bulges/dents) in the sidewall surface of the tyre under inspection. The inspection operation step is described below with reference to FIG. 3 and FIG. 5.

In the inspection operation step, firstly, an original image (inspection image) of the sidewall surface of the tyre under inspection shown in FIG. 5(A) is acquired.

Thereupon, in a coordinates system deviation correcting step (S5) in FIG. 3, deviation in the coordinates system of the inspection image (and principally, phase difference in the circumference direction=angle of rotation) is corrected. As a positional alignment method, phase difference is corrected by image matching so as to coincide with the normal uneven marks (such as logos) present on the sidewall surface.

Thereupon, in a difference processing step (S6) in FIG. 3, a height offset image which has been recorded during teaching is subtracted from the inspection image. This yields a height image of the sidewall surface from which the height of the normal uneven marks has been subtracted.

In the height image obtained in this way, the data of the boundary line portions indicated by the mask image (mask range) does not necessarily indicate suitable values, and therefore the boundary line portions are interpolated on the basis of the mask image in such cases. This interpolation process is described below.

For example, if the mask range in the circumference direction on one line corresponds approximately to several points in terms of continuous X coordinate values, then linear interpolation is performed by determining the average height coordinate of two positions on either side of the mask range of the mask image, in other words, the average height coordinate value of either end of the normal uneven mark, and adopting this average height coordinate as the height coordinate value of the mask range.

On the other hand, if the mask range in the circumference direction continues for several tens of points or more in terms of the X coordinate values, for instance, then all of the height coordinates in the mask range are interpolated by selecting the maximum value or the minimum value of the height pixel values in the mask range of the mask image, within a partial range which is equal to or smaller than the length of the mask range, and adopting the selected height coordinate value as the height coordinate for the mask range.

The processing described above yields an image from which text unevennesses have been excluded, as shown in FIG. 5(D).

The shape defect inspecting step (S7) in FIG. 3 is carried out using this image from which the text unevennesses have been excluded. In the image from which text unevennesses have been excluded which is shown in FIG. 5(D), only the height variation of the normal uneven marks is excluded, and the height of convex defect which is indicated by the white elliptical shape on the left-hand side of the image is left unchanged in comparison with the original image in FIG. 5(A) (inspection image). In this way, in the shape defect inspecting step (S7), a convex defect or a concave defect which remains in the image after excluding text unevennesses is detected.

For the shape defect inspecting step (S7), it is possible to employ an existing image processing method. It is also possible to employ defect extraction based on binarization or defect extraction based on pattern matching.

By using the tyre shape inspection method according to the present embodiment as described above, it is possible to reliably inspect irregular defects (convex defect/bulge, concave defect/dent) having a height variation similar to that of marks which are normal unevennesses (text, logos, patterns, etc.) present in the sidewall surface of a tyre, without being affected by these normal uneven marks. In particular, in tyre shape inspection, it is possible to inspect the shape of a tyre without being affected by deformations which are intrinsic to rubber products, or deformations caused when the tyre is inflated with air, or the like.

The embodiments disclosed here are examples in all respects and should not be considered as limiting the invention. The scope of the invention is indicated by the claims and not by the description of the embodiments given above, and furthermore, the invention is intended to include all modifications within equivalent range and meaning to the scope of the claims.

For example, it is possible for various steps such as the mask image generating step (S2) and the height offset image generating step (S3) to be carried out automatically, or to be carried out manually by an operator while referring to an image. Furthermore, the respective steps may be repeated a plurality of times.

More specifically, in the image processing device 5, the inspection image, the mask image, the height offset image and the image after excluding normal uneven marks, are displayed either in parallel or in switchable fashion, in such a manner that an operator can check each image to see if boundary lines that should be connected are broken, as well as checking if unsuitable portions have been recognized as boundary lines.

Supposing that the checking operation shows a problem location in the mask image, the operator adds or deletes boundary lines via the GUI, and after this correction, the mask image is recalculated. Next, the set height offset image is checked to see whether or not the one type of fixed height value set for each level is abnormal. If there is a problem location, then a corrected region is specified, the height offset value is changed (incremented or decremented by 1 at a time), and after this correction, the height offset image is recalculated.

The image after excluding the normal uneven marks shows the planarized state in the case of actual on-line inspection on the basis of the currently set teaching information, and if there is a problem location upon checking the height image after processing, desirably, the operation of checking and correcting the mask image or the height offset image is carried out again, and these images are respectively corrected and recalculated.

The mask image generated by the present embodiment may include a mask range (mask region) which is larger than the irregular defects (bulges/dents) that are to be detected. If there are irregular defect in a large mask range of this kind, then the irregular defects that are to be detected may be overlooked due to being masked. Therefore, it is desirable to provide processing for interpolating height coordinate values. More desirably, the interpolation processing of the mask range is changed in accordance with the size (length) of the mask range.

Therefore, the interpolation processing (interpolating step) which is carried out after the difference processing step (S6) in FIG. 3 described above will be explained in detail with reference to FIG. 8. In FIG. 8, the X axis represents the rotational direction of the tyre (circumference direction) and the Y axis represents the amount of height variation of the tyre surface.

Figure 8A:
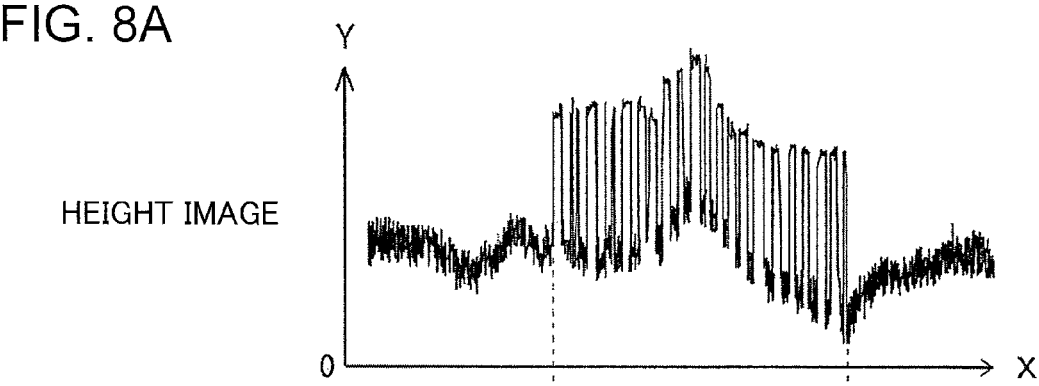
FIGS. 8A to 8E are diagrams showing a method of interpolating height pixel values for positions corresponding to a mask range, in a tyre shape inspection method according to an embodiment of the present invention.

As described previously, in the difference processing step (S6), firstly, a height image of the sidewall surface of the tyre is obtained by subtracting the height offset image recorded during teaching, from the inspection image. FIG. 8A shows one portion of one line of the obtained height image.

In the height image shown in FIG. 8A, there is a large number of normal uneven marks that comprise a small number of pixels in the X axis direction which is the rotational direction of the tyre (short normal uneven marks) and the portions which form the boundary lines of these normal uneven marks, where the height coordinate value (height pixel value) changes suddenly, are close to each other. Therefore, substantially all of the normal uneven mark comes within the mask range in the mask image which is obtained by the mask image generating step shown in FIG. 4A. The mask image obtained in this way is inverted to obtain an inverted mask image.

Figure 8B:

FIG. 8B shows a portion of the inverted mask image thus obtained which corresponds to the height image in FIG. 8A. In the inverted mask image, the value of the binary pixel points in the mask range corresponding to the normal uneven marks in the height image is 0. By finding the logical product of the inverted mask image and the height image in this way, the position corresponding to the mask range in the height image shown in FIG. 8A is masked and the height coordinate value is set to 0, thereby obtaining the masked height image shown in FIG. 8C.

In this masked height image, the height coordinate values of the positions corresponding to the mask range are all zero, and therefore the height coordinate values must be interpolated for the masked positions. The method of interpolating the height coordinate values may employ three interpolation processes: linear interpolation, average interpolation and envelope interpolation. If the position corresponding to the mask range of the masked height image is of a length of approximately several pixels (for example, less than 10 pixels), then the height coordinate value is interpolated by linear interpolation or average interpolation. If the position corresponding to the mask range of the masked height image is of a length exceeding several pixels (for example, 10 or more pixels), then the height coordinate value is interpolated by envelope interpolation.

Figure 8C:
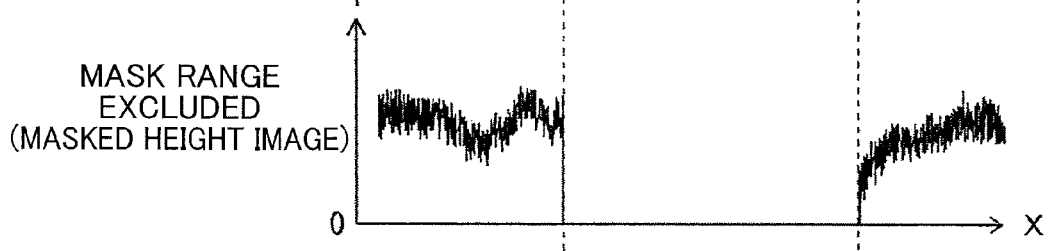
Figure 8D:
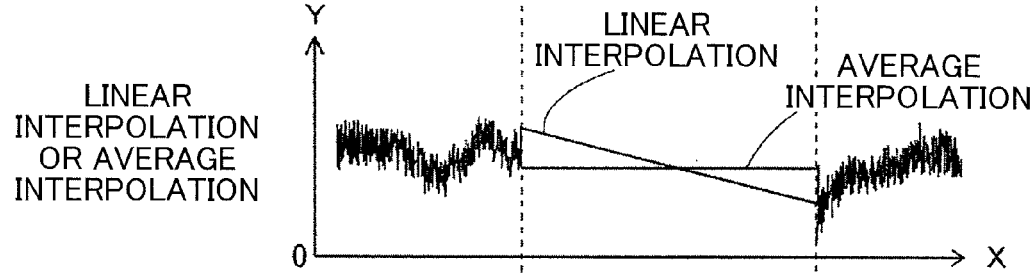

As shown in FIG. 8D, linear interpolation means a method of interpolating by linking the height coordinate values at two positions on either side of a position (region) corresponding to a mask range of the mask image, in other words, the height coordinate values of either end of the normal uneven mark, with a straight line, and allocating the value on the straight line, which changes linearly, as the height coordinate value of the position corresponding to the mask range.

As shown in FIG. 8D, average interpolation means a method of interpolating by finding the average of the height coordinate values at two positions on either side of a position (region) corresponding to a mask range of the mask image, in other words, the average of the height coordinate values of either end of the normal uneven mark, and allocating this average of the height coordinate values (the average height coordinate value) as the height coordinate value of the position corresponding to the mask range.

Figure 8E:
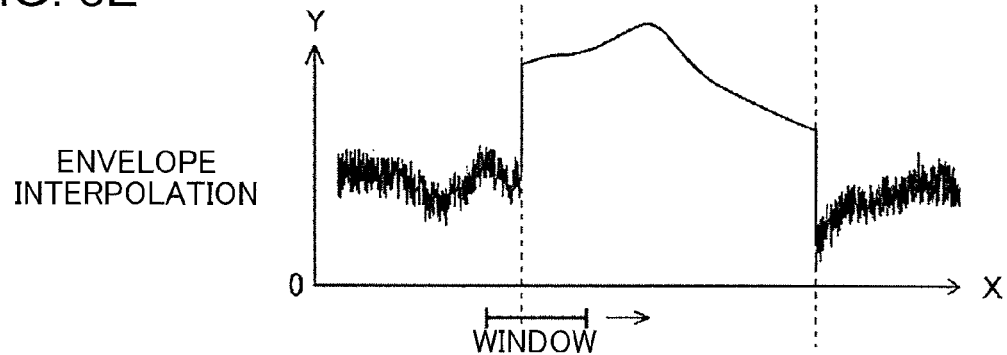

Furthermore, as shown in FIG. 8E, envelope interpolation means a method of interpolation by setting a window as a partial range of the position (region) corresponding to the mask range, in the X axis direction, and allocating the largest height coordinate value in that window range as the height coordinate value of the position corresponding to the mask range. The window in this envelope interpolation is a range which overlaps at least partially with the position corresponding to the mask range, and which is shorter than the mask range and extends in a direction along the mask range (the X axis direction).

The window setting method will now be described in detail. In the following description, it is supposed that the mask range shown in the inverted mask image in FIG. 8B has a length of 40 pixels in the X axis direction, for example. In the height image in FIG. 8A, the point having the smallest X coordinate in the mask range (the leftmost point) is taken as the window center point. A range including the window center point and several pixels to the left and right of the window center point are set as a window on the height image in FIG. 8A. For example, if a window is set by including the window center point and the 10 pixels to the left and right thereof, then the window is set to a length of 21 pixels, with the leftmost point of the mask range being set as the window center point. In general, it is possible for the number of pixels in the window to be substantially half or less than half the number of pixels in the mask range.

The largest height coordinate value in the range of the window set in this way is detected, and the detected value is allocated to the masked height image in FIG. 8C, as the height coordinate value of the position corresponding to the window center point.

Next, the window center point is moved by one pixel in the X axis direction and a new window including the window center point after movement is set by the method described above. The largest height coordinate value in the range of the new window set in this way is detected, and the detected value is allocated to the masked height image as the height coordinate value of the position corresponding to the window center point.

This processing is repeated until the window center point moves to a position corresponding to the point where the X coordinate is largest in the mask range (the rightmost point), and when interpolation is carried out by tracing an envelope with largest height coordinate values, then the height coordinate values can be interpolated through all of the positions corresponding to the mask range. FIG. 8E shows a height image after the envelope interpolation described above and substantially reproduces the approximate form of the profile of the normal uneven marks shown by the height image in FIG. 8A.

In the envelope interpolation described above, the largest height coordinate value in the range of the window is allocated as the height coordinate value for the position corresponding to the window center point, but it is also possible to allocate the smallest height coordinate value as the height coordinate value of the mask range.

When the smallest height coordinate value is allocated, the height image obtained substantially reproduces the approximate shape of the profile of the base portion of the normal uneven marks shown by the height image in FIG. 8A. In other words, regardless of whether the largest height coordinate value or the smallest height coordinate value is allocated, it is still possible to evaluate overall unevenness variation (caused by low-frequency component) in the mask range of the sidewall surface of the tyre. Furthermore, it is also possible to allocate the average of the largest value and the smallest value of the height coordinate values in the range of the window as the height coordinate value of the position corresponding to the window center point.

Outlines of Embodiments

A summary of the embodiment described above is given below.

(1) The tyre shape inspection method according to the present embodiment inspects a shape defect in a sidewall surface of a tyre under inspection, by using an image of a sidewall surface of a sample tyre having the sidewall surface in which uneven marks are formed. The tyre shape inspection method comprises a teaching operation step and an inspection operation step. The teaching operation step comprises: a mask image generating step of detecting boundary lines which are contours of the uneven marks, in a sample original image which is a two-dimensional image of a sidewall surface of the sample tyre, and generating a mask image showing positions of the boundary lines; and a height offset image generating step of generating a height offset image which shows a height of the uneven marks, the height offset image being obtained by, in use of a plurality of discrete height threshold values, classifying a height of regions in the sample original image which remain after excluding regions corresponding to the positions of the boundary lines shown in the mask image; and the inspection operation step comprises: a difference processing step of excluding the uneven marks from an inspection image which is a two-dimensional image of the sidewall surface of the tyre under inspection to generate an unevenness-excluded image, by subtracting the height offset image from the inspection image; and a shape defect inspecting step of inspecting a shape defect in the sidewall surface of the tyre under inspection, on the basis of the unevenness-excluded image.

In this method, it is possible reliably to inspect irregular defects in a sidewall surface of a tyre, without being affected by normal uneven marks (text, logos, patterns, etc.) which are present in the sidewall surface.

(2) Here, in the mask image generating step, the mask image may be generated by obtaining a differential image in which portions of the boundary lines of the uneven marks are emphasized through applying a differential filter, and binarizing the differential image through applying a prescribed threshold value to the differential image thus obtained.

By using a differential filter as in this composition, inspection is not liable to be affected by height offset variation, and since a threshold value can be set in the differential direction only, in the binarization threshold value setting, it is possible stably to extract the boundary line portions of uneven marks.

(3) Furthermore, before applying the differential filter, undetected point in the sample original image may be interpolated and the undetected point may be excluded; and the image from which the undetected point has been excluded may be planarized by excluding a curved component of the sidewall surface from the image from which the undetected point has been excluded, on the basis of the profile shape of the sidewall surface.

Accordingly, it is possible to suppress the unexpected occurrence of large differential values when the differential filter is applied, and the detection accuracy of the positions (boundary lines) of the normal uneven marks can be further improved. Furthermore, in this method, since planarization is carried out by excluding a curved component, then it is possible to prevent the differential values from becoming higher due to the curved component, when the differential filter is applied. Furthermore, since the differential values caused by the curved component are difficult to distinguish from differential values at the boundary lines of the normal uneven marks which are the actual object of detection, then desirably, a planarization process is carried out to exclude this curved component from the height image after interpolation of the undetected point (after linear interpolation).

(4) Moreover, in the height offset image generating step, the following steps may be performed using the sample original image, the mask image and the plurality of discrete height threshold values set in respect of the uneven marks: (I) extracting, from the mask image, line data corresponding to one line data in the sample original image on one line along a tyre circumference direction of the sample original image; (II) respectively setting regions demarcated by the boundary lines shown by the line data extracted from the mask image, on the one line data in the sample original image, as one label region; (III) setting a label region which is longest in the circumference direction, of the plurality of label regions, as a height offset value calculation start region, or setting a region having the largest surface area, of the regions demarcated by the boundary lines shown by the mask image, as a height offset value calculation start region; (IV) determining a height difference between label regions in a region pair formed of mutually adjacent label regions, in the plurality of label regions which are aligned sequentially from the calculation start region, the height difference being determined successively for each region pair starting from a region pair including the calculation start region; and (V) setting a height threshold value closest to the height difference of each region pair, of the plurality of discrete height threshold values, as a height offset value for the label region which is posterior in the alignment sequence of the pair of label regions which constitute the region pair; the height offset image being generated by repeating the steps (I) to (V) in respect of all of the line data in the sample original image.

This composition shows one example of a procedure (steps) for generating an offset image. By calculating an offset image by a procedure of this kind, it is possible to generate an accurate offset image.

(5) Furthermore, in the height offset image generating step, the mask image may be superimposed on the height offset image; and in each region surrounded by boundary lines shown by the mask image, the height offset value which occurs most frequently in a region may be set as the height offset value for the whole of each region.

In this composition, by calculating a plurality of line in a two-dimensional fashion, compared to a case where an offset image is generated by one line only, fine errors in the calculation of the offset image can be corrected, and a more stable offset image can be generated.

(6) Furthermore, in the height offset image generating step, line data in the sample original image along the tyre circumference direction of the sample original image may be extracted; a duplicate line may be generated by duplicating the extracted line data and shifting the duplicate line in the brightness height direction; the duplicate line data may be shifted such that a curved line indicating a low-frequency component corresponding to a portion apart from uneven marks in the extracted line data is substantially continuous with a curved line indicating a low-frequency component corresponding to a portion of the uneven marks in the shifted duplicate line, and the corresponding amount of this shift is determined; and the amount of shift may be defined as the discrete height threshold value.

In this composition, it is possible to confirm a degree of matching by shifting a whole line, and not by evaluating each location on the uneven mark sections, one by one, and therefore fine microscopic errors produced during the specification of the offset value can be reduced.

(7) Furthermore, in the height offset image generating step, a height dimension value of the uneven mark obtained from a design drawing or mold CAD data of the sample tyre, or an actual measurement value of a height dimension of an uneven mark of the sample tyre, may be defined as the discrete height threshold value.

By using CAD data or an actual measurement value of a height dimension as in this composition, it is possible to generate an offset image based on more quantitative dimensional indicators.

(8) The inspection operation step may further comprise an interpolating step of interpolating a height coordinate value in a mask range which has been masked with the mask image used in the difference processing step, in an image obtained by the difference processing step.

In this method, since the interpolating step is provided, then it is possible to suppress overlooking of irregular defects (bulges/dents) that are to be detected, even if there is a mask range (mask region) larger than the irregular defects to be detected, in the generated mask image.

The following methods are given as specific examples of an interpolating step.

(9) For example, in the interpolating step, the height coordinate value may be interpolated by selecting height coordinate values at two positions on either side of the mask range, and allocating a height coordinate value, which is obtained by linear change from one height coordinate value to the other coordinate value, to the mask range.

(10) Furthermore, in the interpolating step, the height coordinate value may be interpolated by selecting height coordinate values at two positions on either side of the mask range, and allocating a height coordinate value, which is obtained by determining an average value of the one height coordinate value and the other coordinate value, to the mask range.

(11) Moreover, in the interpolating step, the height coordinate value may be interpolated by providing a window, which extends in a direction along the mask range, and which overlaps at least partially with the mask range and is shorter than the mask range, and by selecting a largest height coordinate value or a smallest height coordinate value of positions corresponding to the window in the inspection image, and allocating the selected height coordinate value to the mask range, while moving the window from one end to another end of the mask range.

The processing method for interpolating the mask range may be varied depending on the size (length) of the mask range. For example, it is possible to select the method in such a manner that, if the mask range is small (short), then the height coordinate value is interpolated using linear interpolation as described in (9) above or average interpolation as described in (10) above, and if the mask range is large (long), then the height coordinate value is interpolated using envelope interpolation as described in (11) above.

(12) The tyre shape inspection device according to the present embodiment inspects a shape defect in a sidewall surface of a tyre under inspection, by using an image of a sidewall surface of a sample tyre having the sidewall surface in which uneven marks are formed. The tyre shape inspection device comprises: an imaging unit which captures a two-dimensional image of the sidewall surface; a mask image generating unit which detects boundary lines which are contours of the normal uneven marks, in a sample original image which is a two-dimensional image of the sidewall surface of the sample tyre, and generates a mask image showing the positions of the boundary lines; a height offset image generating unit which generates a height offset image which shows a height of the uneven marks, the height offset image being obtained by, in use of a plurality of discrete height threshold values, classifying a height of regions in the sample original image which remain after excluding regions corresponding to the positions of the boundary lines shown in the mask image; a difference processing unit which generates an unevenness-excluded image by excluding the uneven marks from an inspection image, which is a two-dimensional image of a sidewall surface of the tyre under inspection, by subtracting the height offset image from the inspection image; and a shape defect inspecting unit which inspects the shape defect in the sidewall surface of the tyre under inspection, on the basis of the unevenness-excluded image.

With this device, it is possible reliably to inspect irregular defects in a sidewall surface of a tyre, without being affected by normal uneven marks (text, logos, patterns, etc.) which are present in the sidewall surface.

(13) Here, the imaging unit may comprise: a line light irradiating unit which irradiates one light-section beam onto the sidewall surface; an imaging camera which captures an image (reflected light) of the line light irradiated onto the sidewall surface; and an imaging memory which composes a two-dimensional image of the sidewall surface by successively storing one-line images captured by the imaging camera.

EXPLANATION OF REFERENCE NUMERALS 1 tyre shape inspection device
2 tyre rotating machine
3a, 3b sensor unit
4 encoder
5 image processing device
6 imaging camera
7 line light source
8 camera lens
9 imaging element

The invention claimed is:

1. A tyre shape inspection method for inspecting defect in a sidewall surface of a tyre under inspection, by using an image of a sidewall surface of a sample tyre having the sidewall surface in which uneven marks are formed,
the method comprising:
a teaching operation step; and
an inspection operation step,
wherein the teaching operation step comprises:
a mask image generating step of detecting boundary lines which are contours of the uneven marks, in a sample original image which is a two-dimensional image of the sidewall surface of the sample tyre, and generating a mask image showing positions of the boundary lines; and
a height offset image generating step of generating a height offset image which shows a height of the uneven marks, the height offset image being obtained by, in use of a plurality of discrete height threshold values, classifying a height of regions in the sample original image which remain after excluding regions corresponding to the positions of the boundary lines shown in the mask image, and
the inspection operation step comprises:
a difference processing step of excluding the uneven marks from an inspection image which is a two-dimensional image of the sidewall surface of the tyre under inspection to generate an unevenness-excluded image, by subtracting the height offset image from the inspection image; and
a shape defect inspecting step of inspecting the shape defect in the sidewall surface of the tyre under inspection, on the basis of the unevenness-excluded image,
wherein, in the height offset image generating step,
the following steps are performed using the sample original image, the mask image and the plurality of discrete height threshold values set in respect of the uneven marks:
(I) extracting, from the mask image, line data corresponding to one line data in the sample original image along a tyre circumference direction of the sample original image;
(II) respectively setting regions demarcated by the boundary lines shown by the line data extracted from the mask image, on the one line data in the sample original image, as one label region;
(III) setting a label region which is longest in the circumference direction, of the plurality of label regions, as a height offset value calculation start region, or setting a region having the largest surface area, of the regions demarcated by the boundary lines shown by the mask image, as a height offset value calculation start region;
(IV) determining a height difference between label regions in a region pair comprising mutually adjacent label regions, in the plurality of label regions which are aligned sequentially from the calculation start region, the height difference being determined successively for each region pair starting from a region pair including the calculation start region; and
(V) setting a height threshold value closest to the height difference of each region pair, of the plurality of discrete height threshold values, as a height offset value for the label region which is posterior in the alignment sequence of the pair of label regions which constitute each region pair,
the height offset image being generated by repeating the steps (I) to (V) in respect of all of line data in the sample original image.

2. The tyre shape inspection method according to claim 1, wherein, in the height offset image generating step,
the mask image is superimposed on the height offset image; and
in each region surrounded by boundary lines shown by the mask image, the height offset value which occurs most frequently in each region is set as the height offset value for the whole of each region.

3. The tyre shape inspection method according to claim 1, wherein, in the height offset image generating step,
a height dimension value of the uneven mark obtained from a design drawing or mold CAD data of the sample tyre, or an actual measurement value of a height dimension of an uneven mark of the sample tyre, is defined as the discrete height threshold value.

4. The tyre shape inspection method according to claim 1, wherein the inspection operation step further comprises an interpolating step of interpolating a height coordinate value in a mask range which has been masked with the mask image used in the difference processing step, in an image obtained by the difference processing step.

5. The tyre shape inspection method according to claim 4, wherein, in the interpolating step, the height coordinate value is interpolated by selecting height coordinate values at two positions on either side of the mask range, and allocating a height coordinate value, which is obtained by linear change from one height coordinate value to the other coordinate value, to the mask range.

6. The tyre shape inspection method according to claim 4, wherein, in the interpolating step, the height coordinate value is interpolated by selecting height coordinate values at two positions on either side of the mask range, and allocating a height coordinate value, which is obtained by determining an average value of the one height coordinate value and the other coordinate value, to the mask range.

7. The tyre shape inspection method according to claim 4, wherein, in the interpolating step, the height coordinate value is interpolated by providing a window which extends in a direction along the mask range, and which overlaps at least partially with the mask range and is shorter than the mask range, and by selecting a largest height coordinate value or a smallest height coordinate value of positions corresponding to the window in the inspection image, and allocating the selected height coordinate value to the mask range, while moving the window from one end to another end of the mask range.

8. A tyre shape inspection method for inspecting a shape defect in a sidewall surface of a tyre under inspection, by using an image of a sidewall surface of a sample tyre having the sidewall surface in which uneven marks are formed,
the method comprising:
a teaching operation step; and
an inspection operation step,
wherein the teaching operation step comprises:
a mask image generating step of detecting boundary lines which are contours of the uneven marks, in a sample original image which is a two-dimensional image of the sidewall surface of the sample tyre, and generating a mask image showing positions of the boundary lines; and
a height offset image generating step of generating a height offset image which shows a height of the uneven marks, the height offset image being obtained by, in use of a plurality of discrete height threshold values, classifying a height of regions in the sample original image which remain after excluding regions corresponding to the positions of the boundary lines shown in the mask image, and
the inspection operation step comprises:
a difference processing step of excluding the uneven marks from an inspection image which is a two-dimensional image of the sidewall surface of the tyre under inspection to generate an unevenness-excluded image, by subtracting the height offset image from the inspection image; and
a shape defect inspecting step of inspecting the shape defect in the sidewall surface of the tyre under inspection, on the basis of the unevenness-excluded image,
wherein, in the height offset image generating step,
line data in the sample original image along the tyre circumference direction of the sample original image is extracted;
a duplicate line is generated by duplicating the extracted line data and shifting the duplicate line in the brightness height direction;
the duplicate line data is shifted such that a curved line indicating a low-frequency component corresponding to a portion apart from uneven marks in the extracted line data is substantially continuous with a curved line indicating a low-frequency component corresponding to a portion of the uneven marks in the shifted duplicate line, and the corresponding amount of this shift is determined; and
the amount of shift is defined as the discrete height threshold value.

9. The tyre shape inspection method according to claim 8, wherein the inspection operation step further comprises an interpolating step of interpolating a height coordinate value in a mask range which has been masked with the mask image used in the difference processing step, in an image obtained by the difference processing step.

10. The tyre shape inspection method according to claim 9, wherein, in the interpolating step, the height coordinate value is interpolated by selecting height coordinate values at two positions on either side of the mask range, and allocating a height coordinate value, which is obtained by linear change from one height coordinate value to the other coordinate value, to the mask range.

11. The tyre shape inspection method according to claim 9, wherein, in the interpolating step, the height coordinate value is interpolated by selecting height coordinate values at two positions on either side of the mask range, and allocating a height coordinate value, which is obtained by determining an average value of the one height coordinate value and the other coordinate value, to the mask range.

12. The tyre shape inspection method according to claim 9, wherein, in the interpolating step, the height coordinate value is interpolated by providing a window which extends in a direction along the mask range, and which overlaps at least partially with the mask range and is shorter than the mask range, and by selecting a largest height coordinate value or a smallest height coordinate value of positions corresponding to the window in the inspection image, and allocating the selected height coordinate value to the mask range, while moving the window from one end to another end of the mask range.

13. A tyre shape inspection device for inspecting a shape defect in a sidewall surface of a tyre under inspection, by using an image of a sidewall surface of a sample tyre having the sidewall surface in which uneven marks are formed,
the tyre shape inspection device comprising:
an image capturer which captures a two-dimensional image of the sidewall surface; and
an image processor to which a signal is input from the image capturer,
wherein the image capturer comprises:
a line light irradiator which has a plurality of line light beam sources and irradiates one light-section beam onto the sidewall surface;
an imaging camera which captures an image of the line light irradiated onto the sidewall surface; and
an imaging memory which composes a two-dimensional image of the sidewall surface by successively storing one-line images captured by the imaging camera,
the image processor comprises:
a mask image generator which detects boundary lines which are contours of the uneven marks, in a sample original image which is a two-dimensional image of the sidewall surface of the sample tyre, and generates a mask image showing the positions of the boundary lines;
a height offset image generator which generates a height offset image which shows a height of the uneven marks, the height offset image being obtained by, in use of a plurality of discrete height threshold values, classifying a height of regions in the sample original image which remain after excluding regions corresponding to the positions of the boundary lines shown in the mask image;

a difference processor which excludes the uneven marks from an inspection image which is a two-dimensional image of the sidewall surface of the tyre under inspection to generate an unevenness-excluded image, by subtracting the height offset image from the inspection image; and a shape defect inspector which inspects the shape defect in the sidewall surface of the tyre under inspection, on the basis of the unevenness-excluded image, wherein the height offset image generator performs the following steps using the sample original image, the mask image and the plurality of discrete height threshold values set in respect of the uneven marks:

(I) extracting, from the mask image, line data corresponding to one line data in the sample original image along a tyre circumference direction of the sample original image;

(II) respectively setting regions demarcated by the boundary lines shown by the line data extracted from the mask image, on the one line data in the sample original image, as one label region;

(III) setting a label region which is longest in the circumference direction, of the plurality of label regions, as a height offset value calculation start region, or setting a region having the largest surface area, of the regions demarcated by the boundary lines shown by the mask image, as a height offset value calculation start region;

(IV) determining a height difference between label regions in a region pair comprising mutually adjacent label regions, in the plurality of label regions which are aligned sequentially from the calculation start region, the height difference being determined successively for each region pair starting tin from a region pair calculation start region; and (V) setting a height threshold value closest to the height difference of each region pair, of the plurality of discrete height threshold values, as a height offset value for the label region which is posterior in the alignment sequence of the pair of label regions which constitute each region pair, the height offset image generator generates the height offset image by repeating the steps (I) to (V) in respect of all of line data in the sample original image.

* * * * *